(12) United States Patent
Delgado et al.

(10) Patent No.: US 8,904,873 B2
(45) Date of Patent: *Dec. 9, 2014

(54) VISUALIZATION OF TESTS ON SWING TYPE CHECK VALVE USING PHASED ARRAY SEQUENCE SCANNING

(75) Inventors: Jesse R. Delgado, San Antonio, TX (US); Hector Diaz, San Antonio, TX (US)

(73) Assignee: IHI Southwest Technologies, Inc., San Antonio, TX (US)

( * ) Notice: Subject to any disclaimer, the term of this patent is extended or adjusted under 35 U.S.C. 154(b) by 282 days.

This patent is subject to a terminal disclaimer.

(21) Appl. No.: 13/420,066

(22) Filed: Mar. 14, 2012

(65) Prior Publication Data

US 2012/0180570 A1 Jul. 19, 2012

Related U.S. Application Data

(63) Continuation-in-part of application No. 12/965,575, filed on Dec. 10, 2010, now Pat. No. 8,453,508.

(51) Int. Cl.
*G01N 29/04* (2006.01)
*G01N 29/26* (2006.01)

(52) U.S. Cl.
CPC ...... *G01N 29/262* (2013.01); *G01N 2291/2698* (2013.01); *G01N 2291/106* (2013.01)
USPC .................................. 73/618; 73/620; 73/625

(58) Field of Classification Search
CPC . F16K 37/0083; F16K 37/0075; F16K 37/00; G01F 1/7082; G01F 1/712; G01S 15/88
USPC ................... 73/592, 596–600, 602, 618–620, 73/624–625, 627–630, 642, 644
See application file for complete search history.

(56) References Cited

U.S. PATENT DOCUMENTS

| | | | | |
|---|---|---|---|---|
| 4,920,802 A * | 5/1990 | McMullin et al. | | 73/597 |
| 4,977,778 A * | 12/1990 | Nafziger et al. | | 73/597 |
| 6,637,267 B2 * | 10/2003 | Fiebelkorn et al. | | 73/587 |
| 6,666,093 B2 * | 12/2003 | Morganti | | 73/587 |
| 8,115,672 B2 * | 2/2012 | Nouvel et al. | | 342/118 |
| 8,453,508 B2 * | 6/2013 | Delgado et al. | | 73/618 |
| 2001/0037670 A1 * | 11/2001 | Boger et al. | | 73/1.72 |
| 2009/0240453 A1 * | 9/2009 | Straub, Jr. | | 702/79 |
| 2010/0058880 A1 * | 3/2010 | Moody | | 73/865.9 |

* cited by examiner

*Primary Examiner* — Helen Kwok
(74) *Attorney, Agent, or Firm* — Gunn, Lee & Cave, P.C.

(57) ABSTRACT

Computers with proper programs generate signals in phased array sequence. In pulsers with delays, signals are fed through a multiplexor into multiple water wedges that are attached to a valve being tested. For a sequential operation of the valves from the open to the closed position, ultrasonic signals are transmitted through fluid contained in the valve and reflected back through piezo-electric crystals to the multiplexor. By summation and merger of the signals, an image can be developed of the operation of the valve to determine if the valve is operating properly. By using multiple water wedges and pass visualization software, the operator can see exactly how the valve is functioning, which information can be stored for inspections or maintenance.

4 Claims, 13 Drawing Sheets

VISUALIZATION OF TESTS ON SWING TYPE CHECK VALVE USING PHASED ARRAY SEQUENCE SCANNING

CROSS-REFERENCE

This is a continuation-in-part of prior U.S. patent application Ser. No. 12/965,575, filed on Dec. 10, 2010, entitled "Testing of Swing Type Check Valves Using Phased Array Sequence Scanning".

BACKGROUND OF THE INVENTION

1. Technical Field

This invention relates to the non-intrusive testing of valves and, more particularly, to visualization tests on swing-type check valves using phased array sequence scanning.

2. Brief Description of the Prior Art

In the past, if someone wanted to see if a valve was operating properly flow through the valve was the first thing checked. If more information was desired, the valve could be taken apart. As technology advanced, other ways of checking the internal operation of the valve was developed. For example, a magnetic field may be used to determine the position of the disc in a check valve as is shown in U.S. Pat. No. 5,236,011. Also, ultrasonic vibrations have been used to monitor check valves to determine if they are operating properly. Even a combination of acoustic and magnetic techniques have been used in the past to monitor the operation of valves (see U.S. Pat. No. 5,008,841).

Many different techniques of using ultrasonics have been developed to determine either the condition or the position of a valve without taking the valve apart. However, these non-intrusive inspection techniques normally did not give all of the information necessary to determine if a valve is operating properly. For example, the hinge pin on which the clapper of a check valve operates may be worn over a period of time. If this condition is not detected before the hinge pin breaks, a catastrophic failure would result. Typical non-intrusive inspection techniques are not able to detect wear on the hinge pin of a disc-type check valve.

In the last few years, the use of phased arrays to generate a wave front of ultrasonic signals has been used in different types of inspection techniques. For example, phased array has been used to measure flow of a fluid through a pipe as is shown in U.S. Pat. No. 7,503,227. Also variable angle ultrasonic transducers have been used in inspection techniques for pipes, conduit, plates or other foreign metallic members that may have irregularities in the surface of the test member (see U.S. Pat. No. 5,392,652).

As the capability of computers has increased dramatically in recent years, the use of a phased array ultrasonic signal has also been used in the testing of various equipment (see U.S. Patent Publication No. US 2009/0045994 A1). The use of phased array for three-dimensional ultrasonic inspection has also begun to be used in the industry (see U.S. Patent Publication No. US 2009/0293621 A1 and U.S. Pat. No. 7,784, 347). Even combinations of laser beams and ultrasonic signals have been used in maintenance programs for testing equipment (see U.S. Pat. No. 7,728,967). Ultrasonic phased array has been used for some time in the testing of weld joints and pipes (U.S. Pat. No. 7,412,890).

As the nuclear regulatory industry has developed, a need has also developed for a very reliable method for non-intrusive inspection of the valves in a nuclear power plant. The operators needs to know with certainty that the valves are operating properly. Also, the operators need to know if a valve has begun to wear to the point where the valve should be serviced or repaired. This cannot be done with the inspection techniques that have been developed and used in the past.

BRIEF SUMMARY OF THE INVENTION

It is an object of the present invention to provide a non-intrusive inspection technique for valves.

It is another object of the present invention to provide for testing of swing-type check valves using phased array sequence scanning.

It is another object of the present invention to use a non-intrusive technique of phased array sequence scanning to determine if a valve is operating properly and to provide a visualization of the scan.

It is yet another object of the present invention to provide the use of phased array sequence scanning in a non-intrusive technique to test the proper operation of a valve and to provide a visualization of the test for the operator.

It is yet another object of the present invention to provide a water wedge in combination with phased array sequence scanning to test the proper operation of a swing-type check valve by use of a non-intrusive technique.

It is another object of the present invention to use a water wedge to transmit a phased array sequence scanning to a valve full of fluid to test proper operation of the valve.

A further object of the present invention is to use a bonnet water wedge and a body water wedge to each transmit phased array sequence for scanning to determine if the check valve is full of fluid. If not, then locate the position of the air in the check valve.

It is yet another object of the present invention to have two water wedges alternately transmitting phase array sequence scanning to a valve at least partially filled with fluid to properly test operation of the valve.

It is still another object of the present invention to provide visualization of the operation of the check valve using water wedges to transmit phase array sequence scanning to a valve at least partially filled with fluid to properly test operation of the valve.

It is still another object of the present invention to provide a method visualizing operation of a check valve using phase array sequence scanning to test proper operation of the check valve.

A user setup is provided that consists of a computer properly programmed to create a phased array. The phased array is fed through a pulser with delays to a multiplexor. The multiplexor receives the signals from the pulser and creates a serial set of phased array signals, which phased array signals are sent to a plurality of piezo-electric crystals mounted on a water wedge. A water wedge is a wedge-like structure made from a plastic mixture that has the same refraction index as water.

The water wedge is mounted on a steel plate forming the top of a check valve, also called a bonnet. If the check valve is full of liquid, phased array sequence scanning can be used to monitor the operation of the check valve by receiving reflected signals back through the water wedge via receiving piezo-electric crystals, which receiving piezo-electric crystals provide serial input into the multiplexor. The output of the multiplexor sends parallel signals to a receiver with delays, which received signals are summed in a summation device. The summed signals feeds through a phase array acquisition and control to an image development and display. In the image development and display, the operation of the check valve can be monitored to determine if it is operating properly, or if repairs are necessary.

If the check valve under test is not full of fluid, the use of a water wedge to create phase array sequence scanning will not work. For example, an air pocket could be located at the top of the check valve in which case no signal would be transmitted nor received due to the air inside of the check valve. However, this problem can be overcome by having a pair of water wedges on either side of the check valve, typically one on the bonnet and one on the body, each of which would transmit phase array sequence scanning. If a signal is received from the water wedge to the other, there is no air pocket. However, if a signal is not received from one water wedge to the other, there is an air pocket. The location of the air pocket can be determined by time of travel of reflected signals, which reflected signals will reflect off a surface of the fluid adjacent to the air pocket to provide for reflected signals.

By capturing the information received back, a computer-generated image of a check valve and the operation of the check valve can be created. For example, if a check valve is fluttering, it may flutter so fast that a human being could not detect the fluttering. The sequence would have to be slowed down to the point that it could be seen by most persons. The computer would create a graphic illustration of what is happening inside of the check valve.

BRIEF DESCRIPTION OF THE DRAWINGS

The patent or patent application file contains at least one drawing executed in color. Copies of this patent or patent application publication with color drawings(s) will be provided by the Office upon request and payment of the necessary fee.

DESCRIPTION OF THE PREFERRED EMBODIMENT

Figure 1:
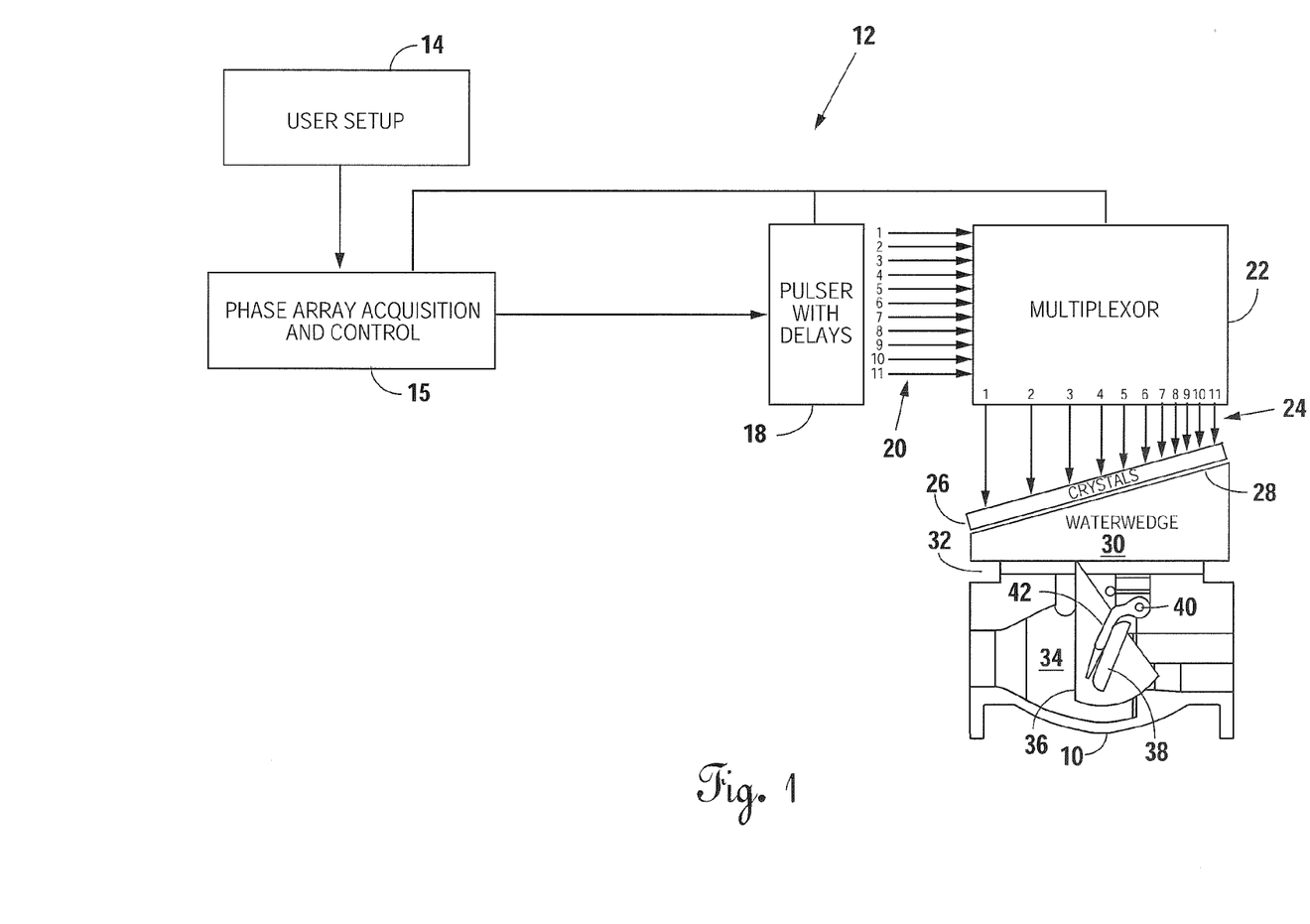
FIG. 1 is a combined pictorial and block diagram illustrating the use of phased array sequence scanning to generate phased array signals in a swing-type check valve.

Referring now to FIG. 1, a swing-type check valve 10 is being tested by phased array sequence scanner illustrated generally by the reference numeral 12. The phased array sequence scanner 12 has a user setup 14 that will include a computer that is programmed to generate a wave front to be used in testing the swing-type check valve 10. If some other type of valve is being tested, the user setup 14 can be varied and the program changed to generate the particular type of wave front desired for the valve under test.

The wave signal from the user setup 14 feeds to a phased array acquisition and control 16. The phased array acquisition and control 16 takes the instructions from the software contained in the user setup 14 and fires the voltages in a timing sequence as determined by the computer program. The signals from the phased array acquisition and control 16 feed through a pulser with delays to generate spike signal voltages 20 that are fed through multiplexor 22. In the illustration as shown in FIG. 1, a total of eleven voltage spike signals 20 are generated, but this number can vary depending upon design of the phased array sequence scanner 12.

The multiplexor 22 manages the outgoing pulses 24 which fires transmit piezo-electric crystals 26. In the present embodiment, because there are eleven spike voltage signals 20 being received from the pulser with delays 18, there will be eleven transmit piezo-electric crystals 26. In this preferred embodiment, the number of piezo-electric crystals 26 is eleven. However, the number of piezo-electric crystals can vary according to the preference of the end user.

The number of piezo-electric crystals could be as few as three, but the upper end is controlled only by the number of discreet signals that can be transmitted and received. Twenty or thirty piezo-electric crystals could be used almost the same as eleven are being used in this preferred embodiment. The piezo-electric crystals can be naturally occurring such as quartz, but man-made lattices that form a piezo-electric crystal are better because of the quality control.

The transmit piezo-electric crystals 26 are attached to the inclined angle 28 of water wedge 30. The inclined angle 28 can vary from 0° to 70°, but Applicant has found approximately 20° to be ideal. Water wedge 30 is not actually made from water, but is made from a plastic mixture that has the same refraction index as water. Also, the water wedge 30 as illustrated in FIG. 1, is not to scale, but is illustrated in a manner that is approximately ten times its actual size when compared to the swing-type check valve 10 located there below. The water wedge 30 is enlarged for illustration purposes only.

During a normal test, the swing-type check valve 10 will be full of liquid. Because the water wedge 30 has the same refraction index as water, during a test, it will appear as if the top plate 32 of a check valve 10 is not present. This gives a much better signal. Therefore, the water wedge 30 is specifically designed to have approximately the same refraction index as the fluid contained inside of swing-type check valve 10.

In normal operation, the user setup 14 with the computer and program contained therein will cause the phased array acquisition and control 16 to generate signals that fed to the pulse with delays 18 that creates timed spike voltage signals 20 that feed through multiplexor 22. From multiplexor 22, the outgoing pulse signals 24 fire the transmit piezo-electric crystals 26 which generate a wave front in water wedge 30. The wave front flows through top plate 32 and into the chamber 34 of swing-type check valve 10. The wave front 36 is illustrated by the pie-shaped shaded area within chamber 34. The wave front 36 encompasses the disc 38 suspended from pin 40 through the disc arm 42. The wave front 36 will be sequenced over time to follow an entire cycle of a disc 38 within swing-type check valve 10.

Figure 2:
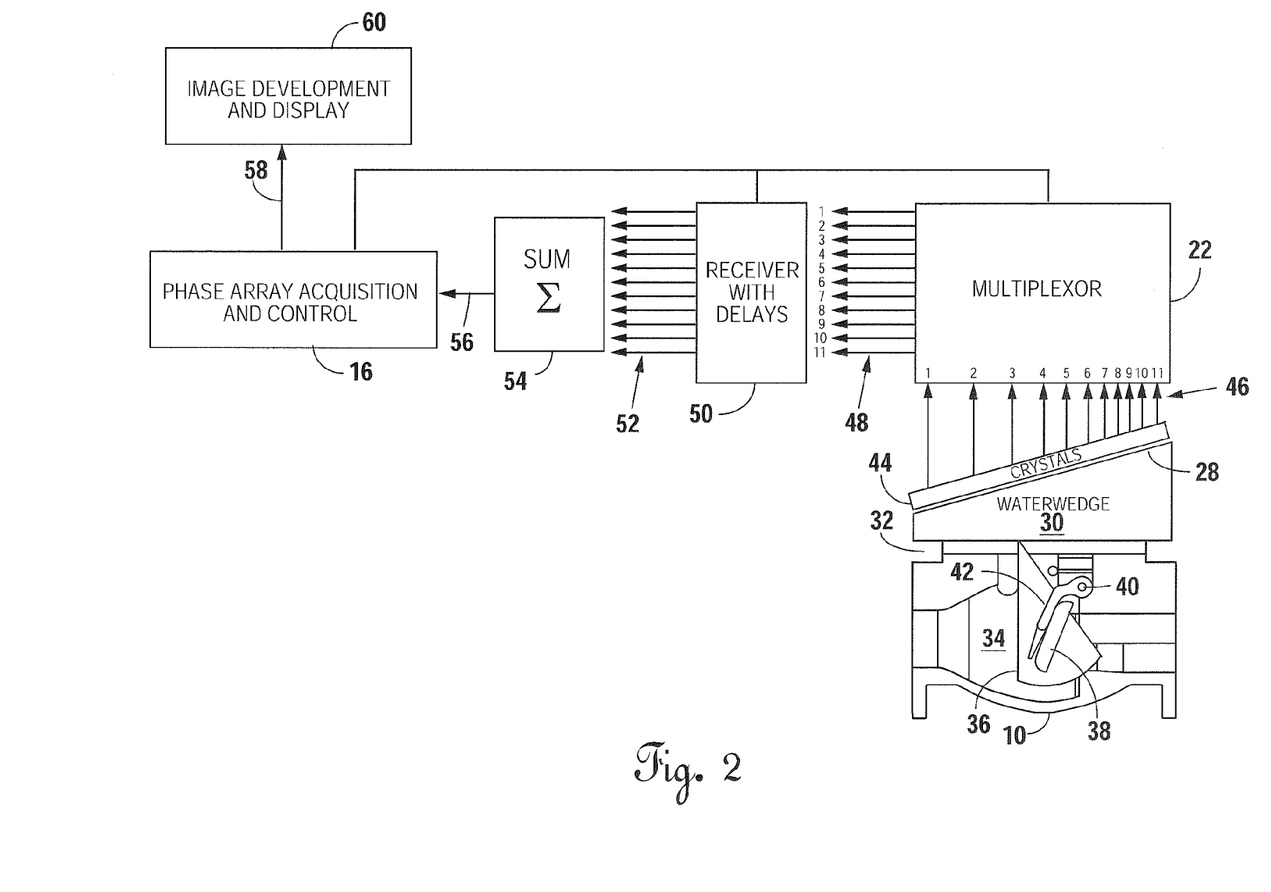
FIG. 2 is a combination pictorial and block diagram using phased array sequence scanning to illustrate the receiving of reflected signals resulting from the phased array sequence scanning.

Referring now to FIG. 2, in response to the wave front 36, acoustic signals will be received back through the top plate 32 and water wedge 30 to the receiving piezo-electric crystals 44. While the same piezo-electric crystal could be used to receive or transmit, in this preferred embodiment, the receiving piezo-electric crystals 44 are different from the transmitting piezo-electric crystals 26. The acoustic signals received via the receiving piezo-electric crystals 44 through water wedge 30 generate reflection signals 46. The reflection signals 46 are processed through multiplexor 22 to generate return parallel signals 48 that feed into receiver with delays 50. From the receiver with delays 50, reflected signals 52 feed into a summation device 54, which gives a summed output 56 to the phased array acquisition and control 16. The phased array acquisition and control 16 provides an image signal 58 to image development and display 60. The image development and display 60 gives a visual image of what is happening inside of swing-type check valve 10 through its normal operation if phased array sequence scanning is used.

The image development and display 60 uses a combination of signal amplitude and timing to form an image as to the operation of a swing-type check valve. Therefore, time of flight of a particular pulse inside of the swing-type check valve 10 is important as well as the amplitude of each signal.

Figures 3, 4:
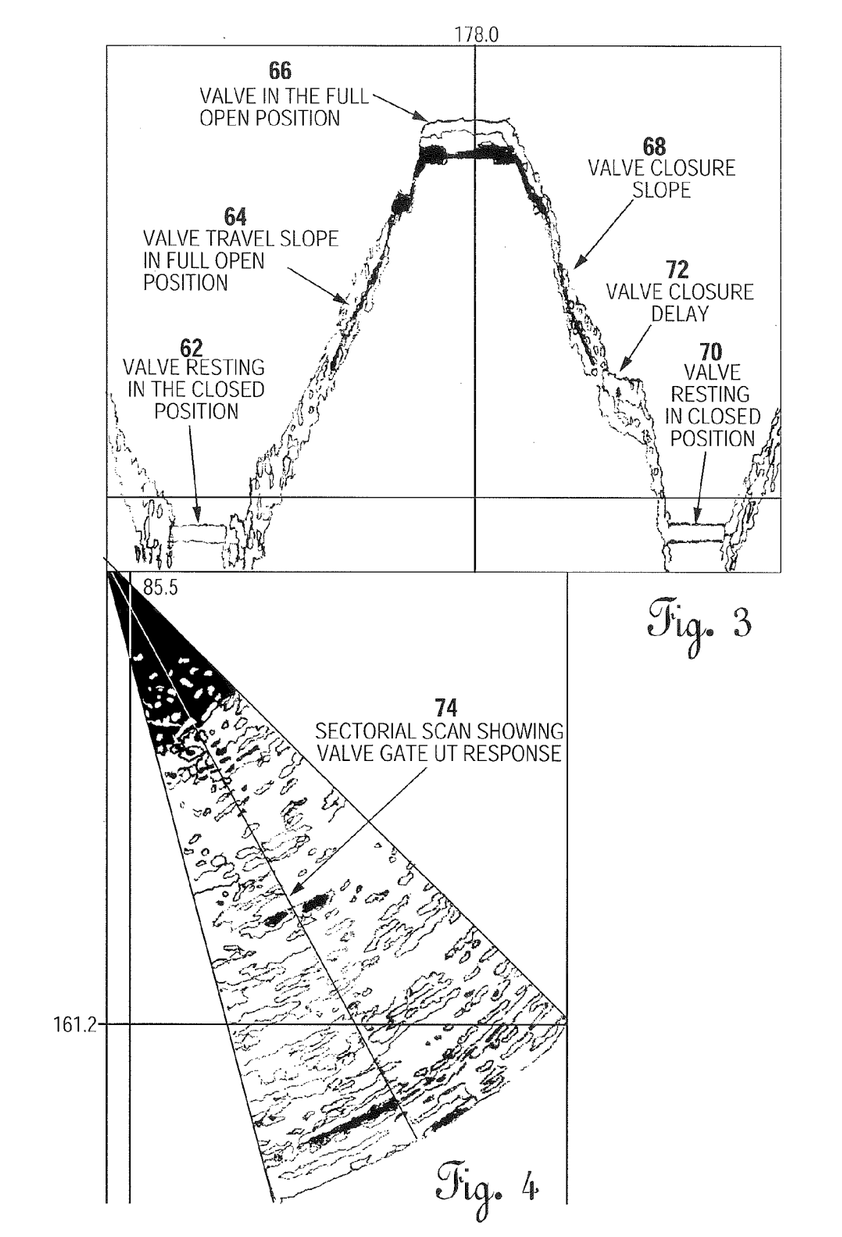
FIG. 3 is a color recording of final data results for an actual swing-type check valve using phased array sequence scanning.
FIG. 4 is a cross-sectional view of the sound beam interacting with the disc of the check valve whose data is shown in FIG. 3.

Referring now to FIG. 3, the image being shown is the image that would be recorded over time during the actual operation of the check valve. If a swing-type check valve is operating properly, a valve closed signal 62 will be generated. As the disc on the valve opens, a valve opening signal 64 shows the travel of the disc when it goes from the closed position to the full open position. When the valve is full open, a valve open signal 66 is generated.

The main signal is associated with the color red. Red means there is a lot energy being returned at that point during the cycle.

During the reverse operation, a valve closing signal 68 is generated which is a downward slope as shown in FIG. 3. When the disc of the swing-type check valve closes, another valve closed signal 70 is generated. However, for the check valve being tested as illustrated in FIG. 3, there is a valve closure delay signal 72 between the valve open signal 66 and the valve closed signal 70. This valve closure delay signal 72 indicates a problem in the valve such as wear of pin 40 shown in previous FIGS. 1 and 2. The valve closure delay signal 72 indicates there is a problem with the valve under test which could be due to wear. Therefore, before a catastrophic failure occurs, the valve should be either repaired or replaced.

By looking at the phased array sequence scanning signal shown in FIG. 3, an operator can quickly tell if (1) the valve being tested is operating properly, (2) the valve being tested is worn or has some other defect and (3) the valve may cause problems in the near future. The signal shown in FIG. 3 is easily understood by the operator.

Referring now to FIG. 4, the pie-shaped figure is actually a cross-sectional view of the sound beam interacting with the valve and valve disc as previously shown in FIG. 3. However, the cross-sectional view shown in FIG. 4 is harder to interpret than the wave form shown in FIG. 3. In FIG. 4, the two red dots 74 actually show the valve gate moving from the full open to the full closed position. It is much more difficult to get meaningful information out of the pie-shaped cross-sectional view shown in FIG. 4, but the image shown in FIG. 3 is easily understood by the operator.

Applicant has found that if the inclined angle 28 of the water wedge 30 is 15°, it provides the good data. The view as shown in FIG. 3 is a volume corrected sound beam at 15°. The sound energy can either be measured at (1) a single angle or (2) all the sound energy can be merged to form one picture. Each has their advantages and disadvantages.

Figure 5:
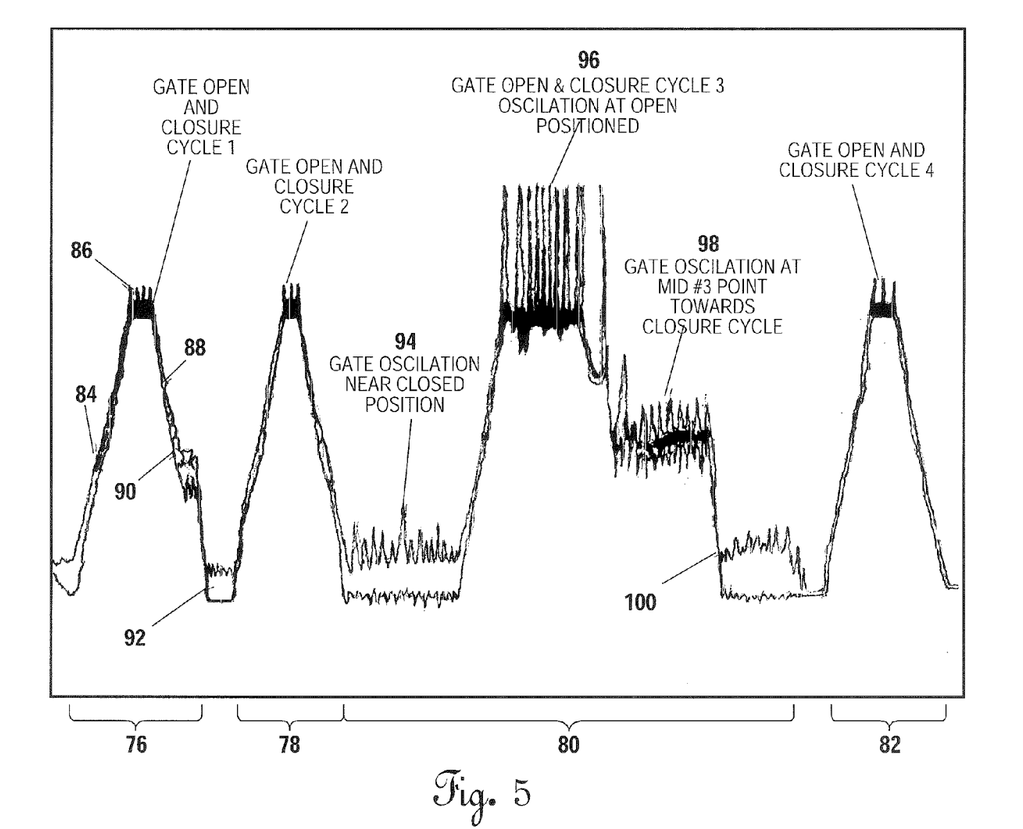
FIG. 5 is an analysis of four different check valves using phased array sequence scanning.

Referring to FIG. 5, the phased array sequence scanning of four different valves 76, 78, 80 and 82 are shown in cycles 1, 2, 3 and 4, respectively. Cycle one for valve 76 has a normal open cycle as is represented by the incline 84. The full open position 86 is also normal for valve 76. During the closing cycle 88, there is a valve closure delay 90 caused by wear inside of valve 76. The valve closure delay 90 is typical of wear in the pin 40 (see FIGS. 1 and 2) of a swing-type check valve. When fully closed, a closed signal 92 will again be given.

Cycle two is for a normally operating swing-type check valve 78 with no signs of undue wear or any other malfunctions.

However, valve 80, as is represented by gate open and closing cycle three has numerous problems. The gate or disc 38 in valve 80 has a tendency to oscillate near the closed position. The gate oscillation is illustrated by reference numeral 94. Also, when fully opened, the valve 80 again has oscillations at the open position as represented by the numeral 96. During the closure cycle of valve 80, there is gate oscillation at a midway position of the valve as represented by numeral 98. Again, when valve 80 is fully closed, there is again gate oscillations at the closed position as indicated by reference numeral 100. The valve 80 as shown in cycle three is about to have a catastrophic failure. During catastrophic failure any of a number of things could occur such as the disc coming off of the hinge pin or other types of similar failure. A valve operating similar to valve 80 should be replaced immediately.

Valve 82 as represented by cycle four is again a normal functioning valve.

As can be seen by looking at FIGS. 3 and 5, when phased array sequence scanning is used in testing swing-type check valves, the operator can easily see if the valve is functioning properly.

For the phased array sequence scanning to operate properly, the valve being tested should be full of liquid. If there is only liquid upstream of the disc, the valve can still be tested but the water wedge would have to be positioned upstream of the hinge point for the disc.

If it is desired to use the phased array sequence scanning on some other type of valve other than a hinged type check valve, a known signal will have to be generated for a good, properly operating valve. Thereafter, in checking similar type valves, future signals would be compared to the known signal to determine if the valve is operating properly.

Figure 6:
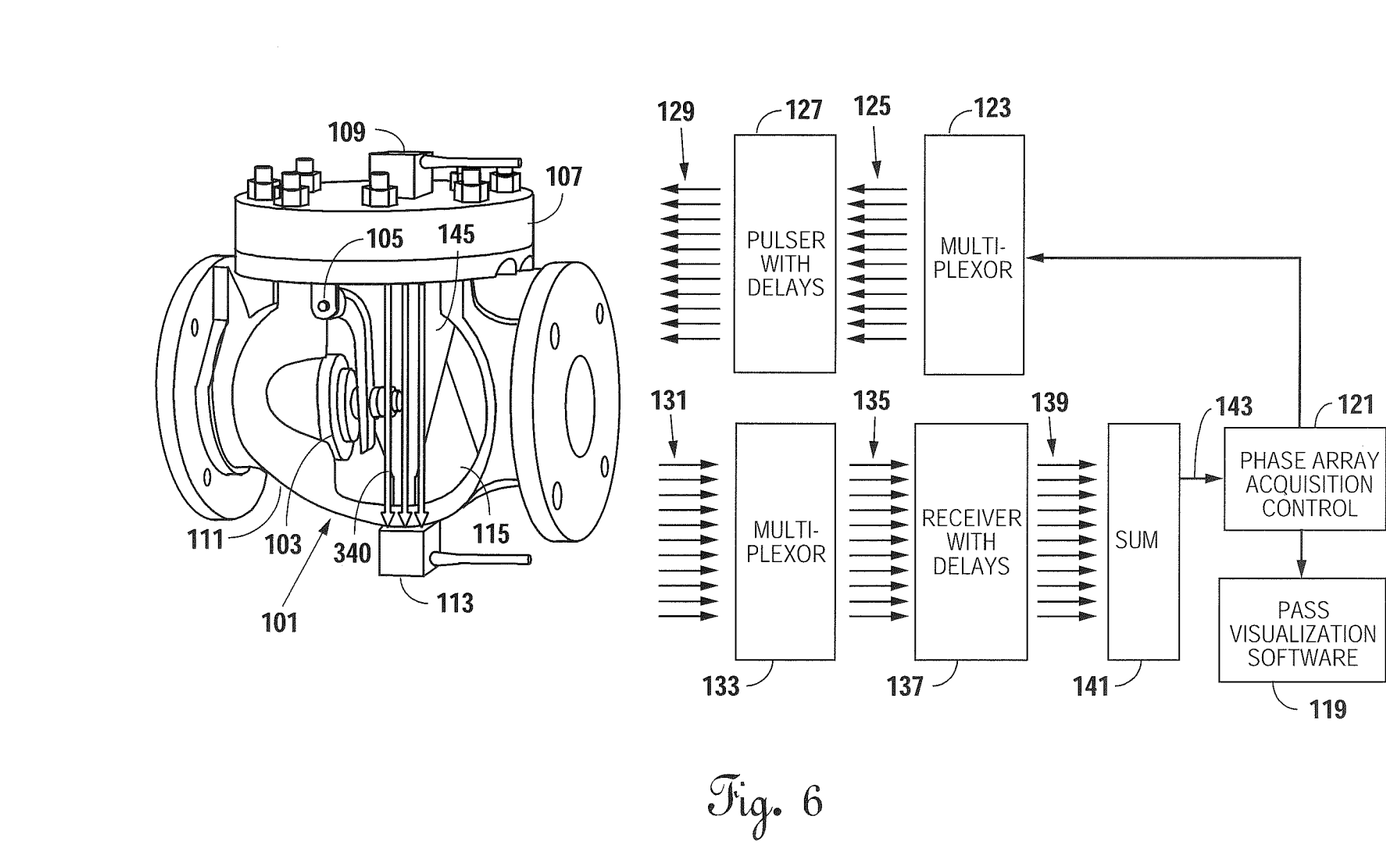
FIG. 6 is a combined pictorial and block diagram illustrating a pulsing probe generating phase array signals in a swing-type check valve and a receiving probe receiving those phase array signals.

Recently, it was discovered that if air exists inside of the swing-type check valve 10, even a small portion under top plate 32, the invention as previously described herein above did not work. As a solution to that problem, in FIG. 6 the swing-type check valve 101 is again pictorially illustrated with a portion cut away for illustration purposes. The swing-type check valve 101 has a clapper 103 pivotally connected on hinge 105 with the direction of flow of the fluid being against the clapper 103 to cause the clapper 103 to open. The top of the swing-type check valve 101 is enclosed by a bonnet 107 (previously referred to herein above as top plate 32). Mounted on the bonnet 107 is a bonnet probe 109. Mounted on the lower part of the body 111 is body probe 113. Bonnet probe 109 and body probe 113 are essentially the same piezoelectric crystals 26 mounted on water wedge 30 as previously described in conjunction with FIGS. 1 and 2. While the position of the bonnet probe 109 and the body probe 113 is not critical, it is important that they oppose each other and that they be capable of generating pulses or receiving pulses from the other probe. In FIG. 6, the pulsing probe is bonnet probe 109. When bonnet probe 109 is pulsed, it generates a wave front 115 moving in the direction of arrows 117 to body probe 113 with body probe 113 being the receiving probe.

The phase array acquisition control 121 sends a signal to the multiplexer 123. The parallel signals 125 feed from multiplexer 123 through pulser with delays 127 to generate phased pulse signals 129. The phased pulse signals 129 are then fed to the bonnet probe 109.

From the body probe 113, received these pulse signals 131 are fed to multiplexer 133. From the multiplexer 133 energy pulses 135 are sent to the receiver with delays 137. From the receiver with delays 137, delayed energy pulses 139 are sent to the summer 141. From the summer 141, then the sum 143 is fed through the phase array acquisition control 121 to the pass visualization software 119. If there is an air gap inside of swing-type check valve 101 no signal will be indicated in sum 143.

While the number of channels can vary, eleven channels have been found to work very effectively.

Figure 7:
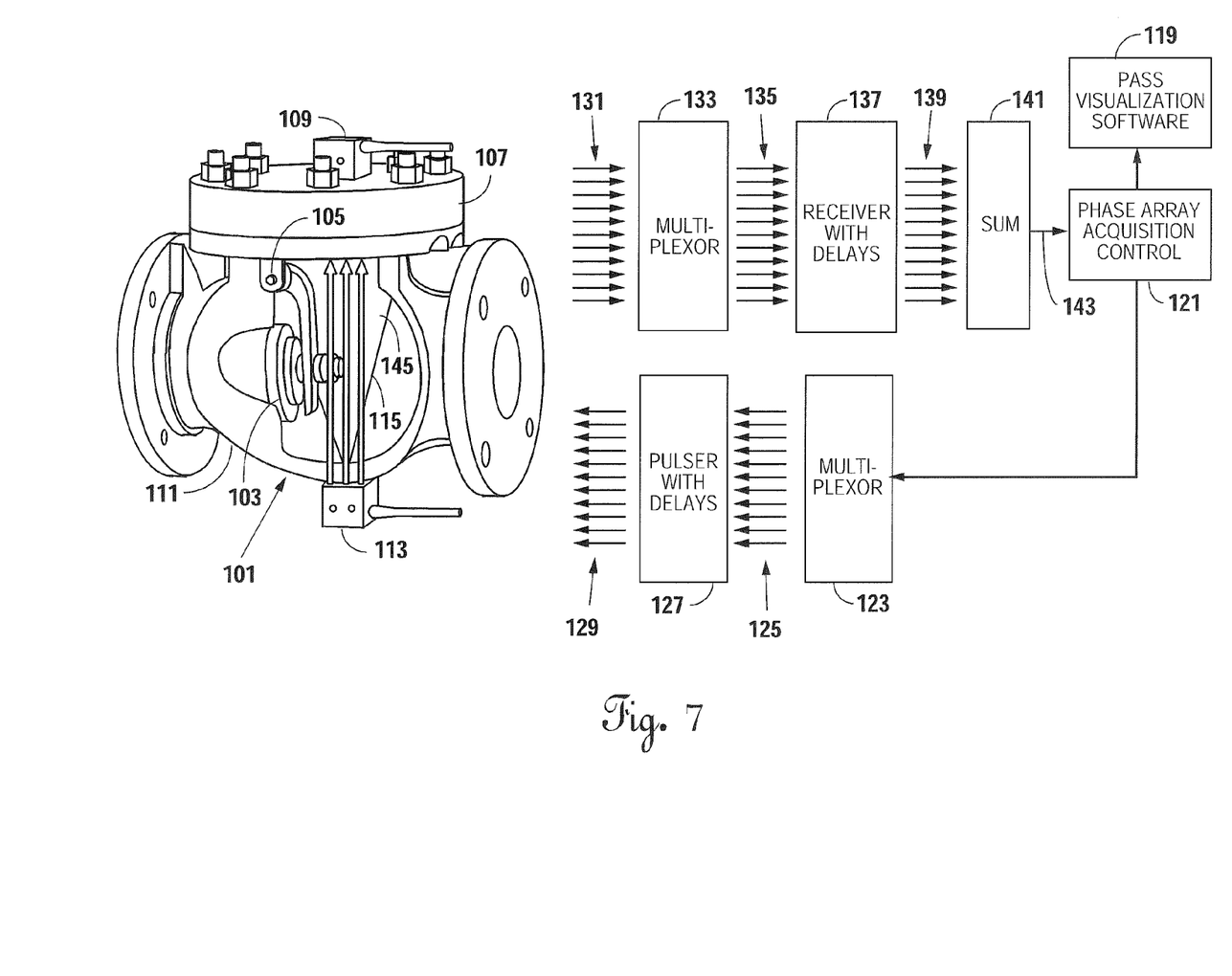
FIG. 7 is the same as FIG. 6, except the function of the receiving probe and the pulsing probe have been reversed.

Referring now to FIG. 7, body probe 113 is now the pulsing probe and bonnet probe 109 is now the receiving probe. Where previously wave front 115 had been generated, now wave front 145 is being generated by the body probe 113. Wave front 145 flows in the direction of arrows 147. Sum 143 is received pursuant to the pulsing signal being created by bonnet probe 109 as shown in FIG. 6 or the pulsing signal being from the body probe 113 as shown in FIG. 7. In either case, there is no air inside of the swing-type check valve 101 to interfere with signal transmission.

Figure 8:
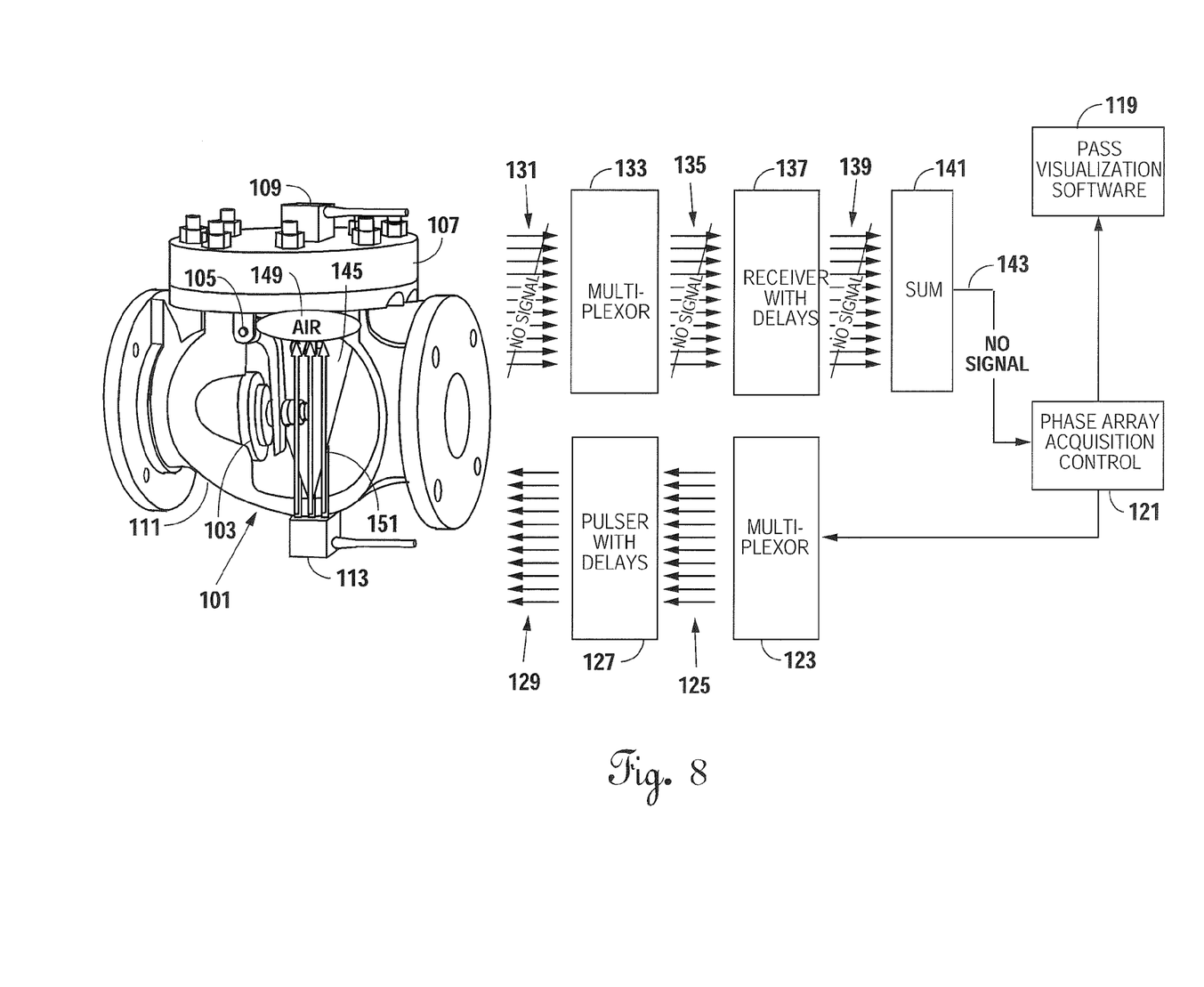
FIG. 8 is a combined pictorial and block diagram illustrating the use of a pulsing probe to generate a phase array signal, but receipt of the phase array signal is blocked at the receiving probe by air gap.

Referring now to FIG. 8, it is operated the same as FIG. 7, except an air gap 149 exists just under the bonnet 107 of the swing-type check valve 101. Therefore, when the body probe 113 generates a wave front 145 in the direction indicated by arrows 151, the wave front does not make it to bonnet probe 109 because of the air gap 149. There will be no received phase pulse signals 131, no energy pulses 135 and no delayed energy pulses 139. This means that there will be no sum 143 being fed to the phase array acquisition control 121. However, when a wave front 145 hits the air gap 149, a return signal will be reflected back due to the air interface of the air gap 149. The reflected signal will be received back by the body probe 113 through an extra channel in the pulser with delays 127 and an extra channel in the multiplexer 123 and sent back to the phased array acquisition control 121. The time of travel of the reflected signal will indicate exactly where the air gap 149 is located. In FIG. 8, the time of travel of the reflected signal will be the greatest because the air gap 149 is immediately below the bonnet 107.

Figure 9:
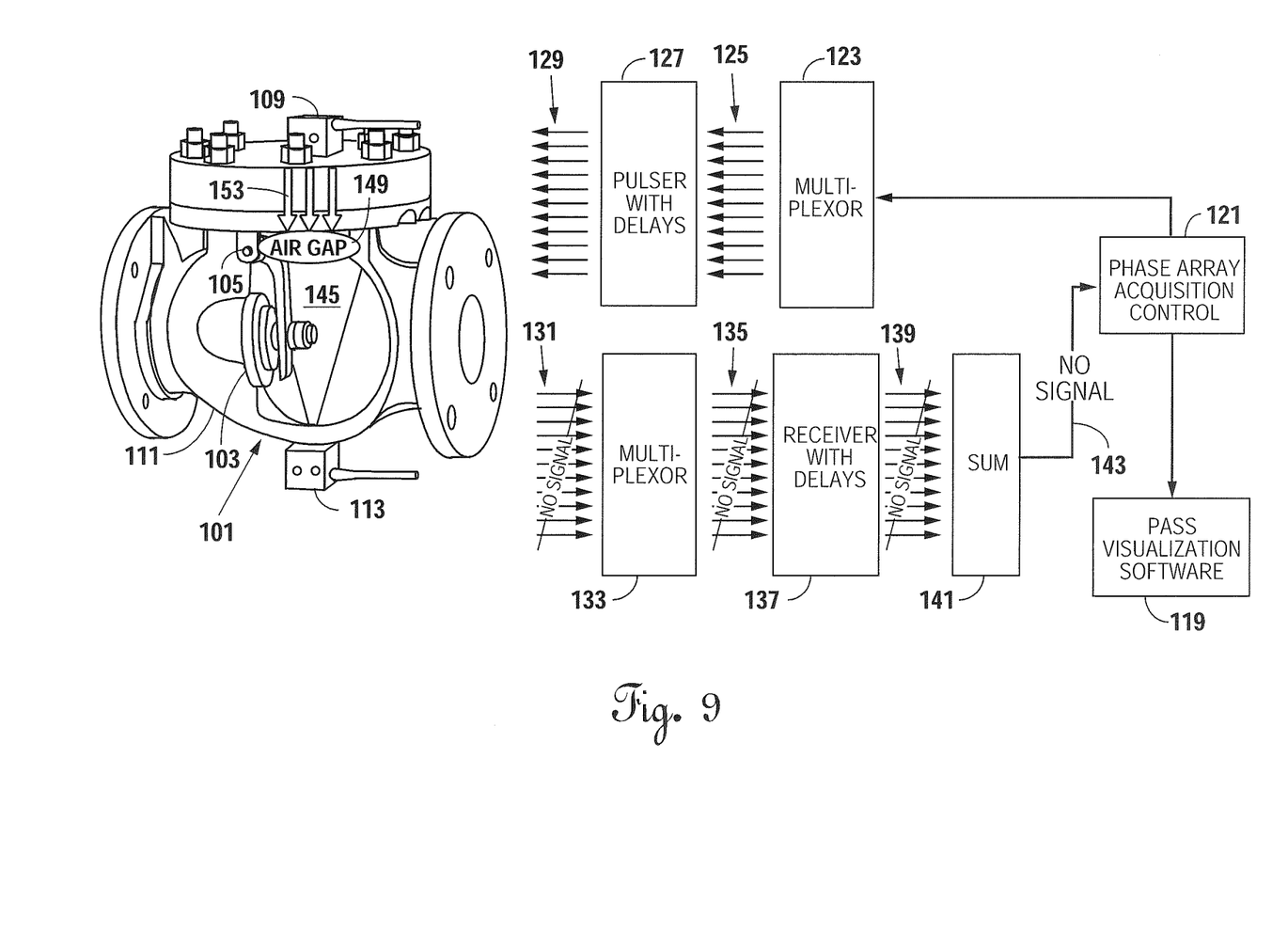
FIG. 9 is the same as FIG. 8, except the function of the pulsing probe and the receiving probe have been reversed.

FIG. 9 is the same as FIG. 8, except the pulsing probe is now bonnet probe 109 and the receiving probe is body probe 113. There will be no wave fronts 145 or 151 in FIG. 9 because the signal is reflected by air gap 149. However, there will be a reflected signal received in an extra channel of bonnet probe 109. The time of travel of the reflected signal will be less than the time of travel as shown in FIG. 8. In that manner, the location of the air gap 149 inside of swing-type check valve 101 can be calculated using the respective time of travel of reflected signals in FIGS. 8 and 9. The arrows 153 in FIG. 9 are much shorter than the arrows 151 in FIG. 8 because their travel distance is much less. It is that travel distance that allows for a determination as to where the air gap 149 is actually located. In FIG. 9 there is no received phased pulse signals 131, no energy pulses 135, no delayed energy pulses 139 and no sum 143.

Figure 10:
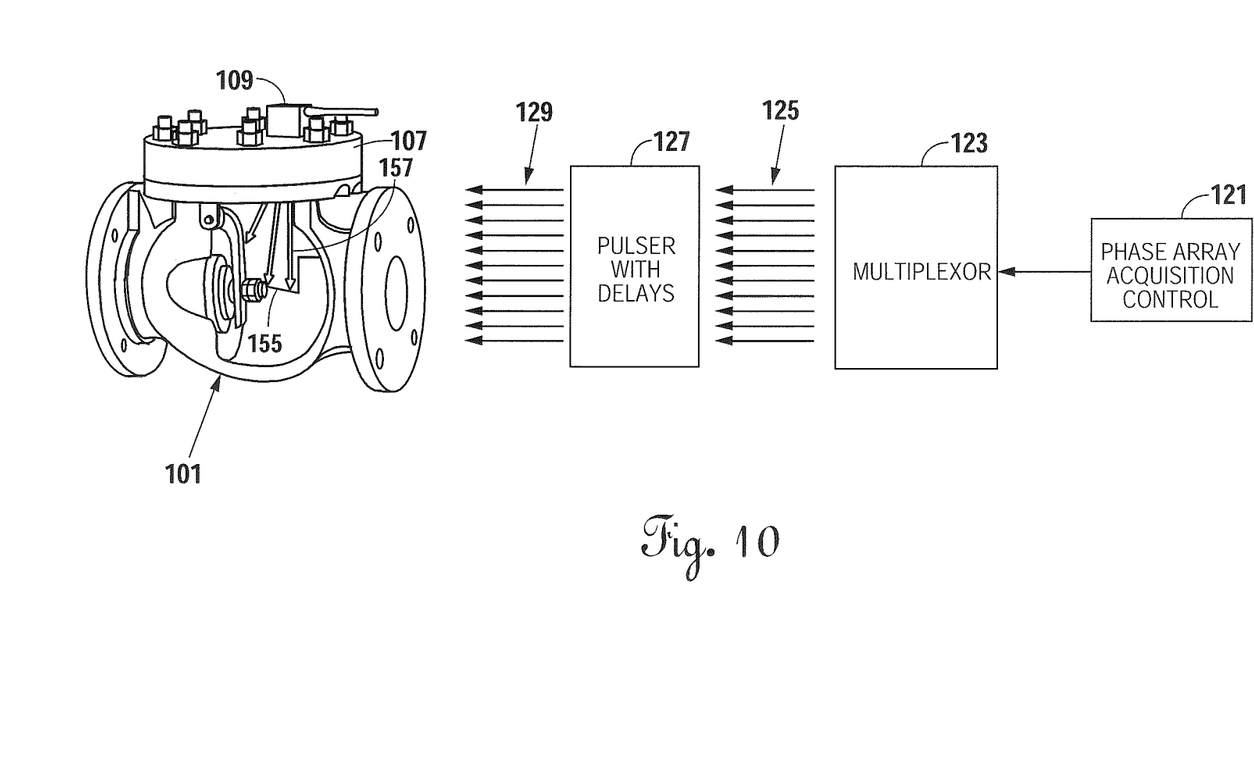
FIG. 10 is a combined pictorial and block diagram illustrating the use of a bonnet probe to generate a phase array signal in a swing-type check valve.
Figure 11:
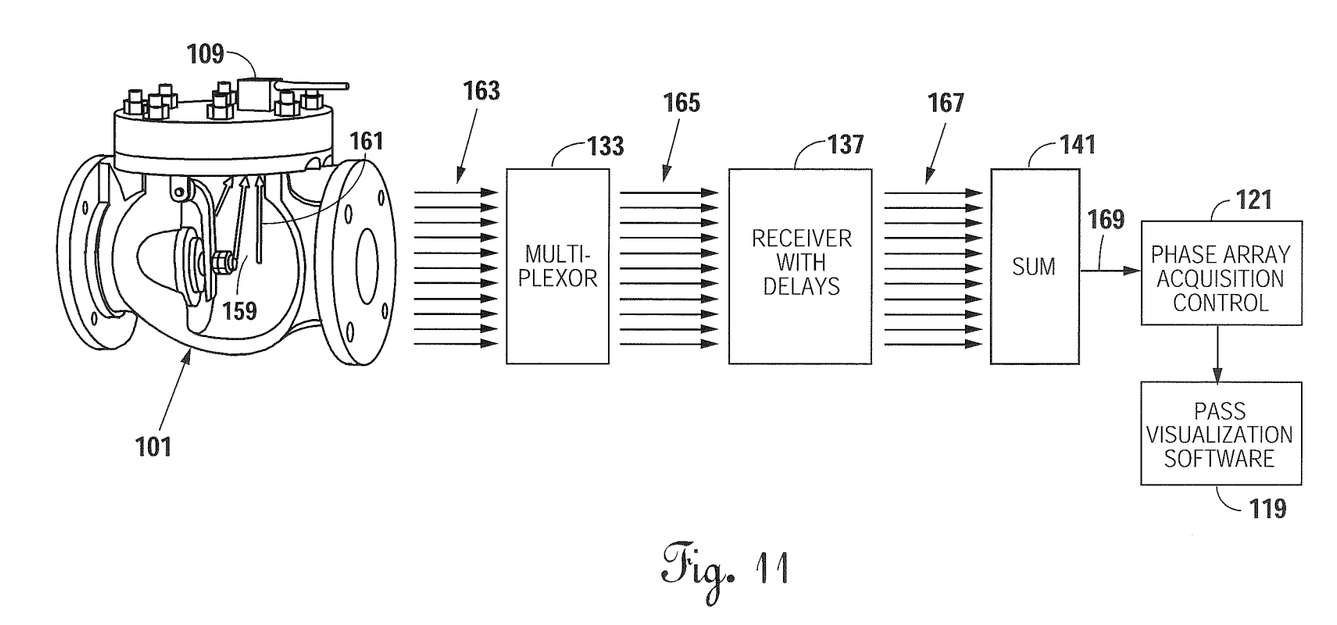
FIG. 11 is a combined pictorial and block diagram illustrating a bonnet probe receiving reflected phase array signals in a swing-type check valve.

Referring now to FIGS. 10 and 11 in sequence, the bonnet probe 109 sends out the scanned pulse data in swing-type check valve 101 in a manner as previously described in connection with FIG. 6, except there is no body probe 113. As shown in FIG. 10, the phase-array acquisition control 121 sends a signal to the multiplexer 123 that generates parallel signals 125 to pulser with delays 127. Pulser with delays 127 sends phased pulse signals 129 to the bonnet probe 109 which generates a wave front 155 in the direction indicated by the arrows 157.

Referring to FIG. 11, the wave front 155 of FIG. 10 is reflected in a reflected wave front 159 as indicated by the reflected arrows 161. The reflected wave front 159 generates through bonnet probe 109 reflected phase pulse signals 163 which are sent to multiplexer 133. From multiplexer 133, the reflected energy pulses 165 are sent to the receiver with delays 137 to give reflected/delayed energy pulses 167 which is fed into a summer 141. From the summer 141, a reflected sum 169 is sent to the phase array acquisition control 21 and on to the pass visualization software 119.

Figure 12:
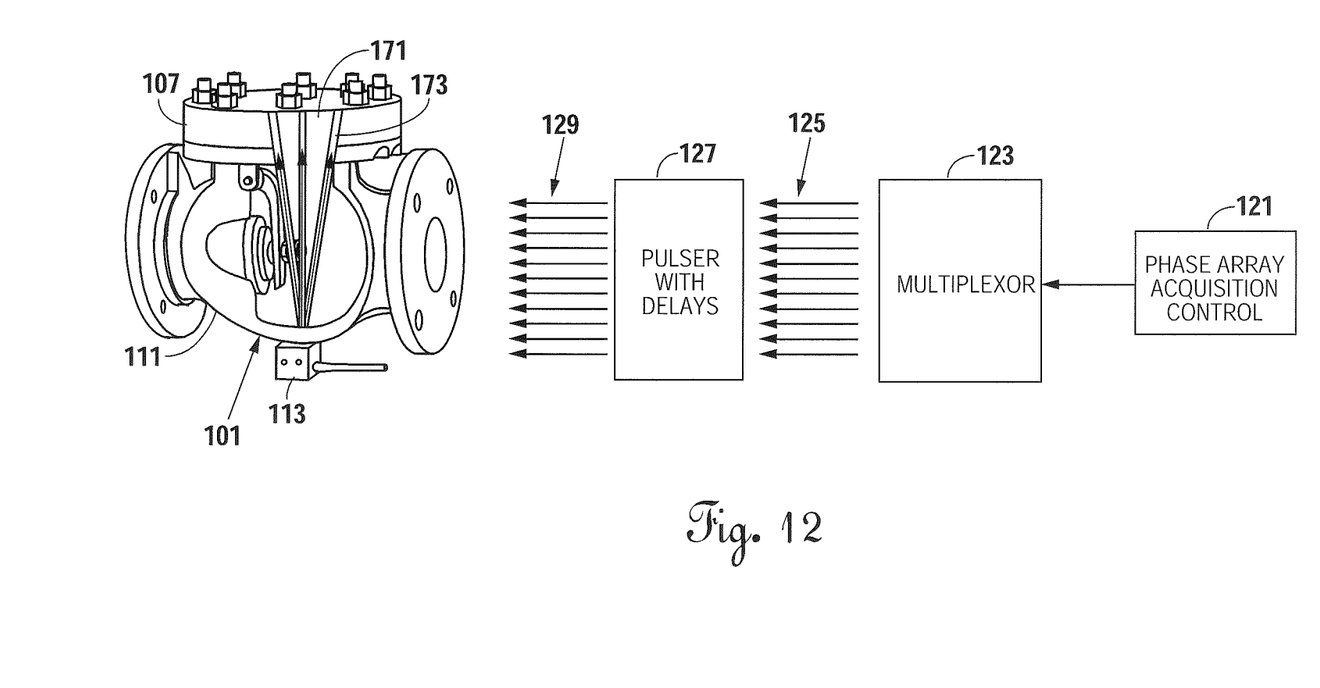
FIG. 12 is a combined pictorial and block diagram illustrating the use of a body probe to generate a phase array signal in a swing-type check valve.
Figure 13:
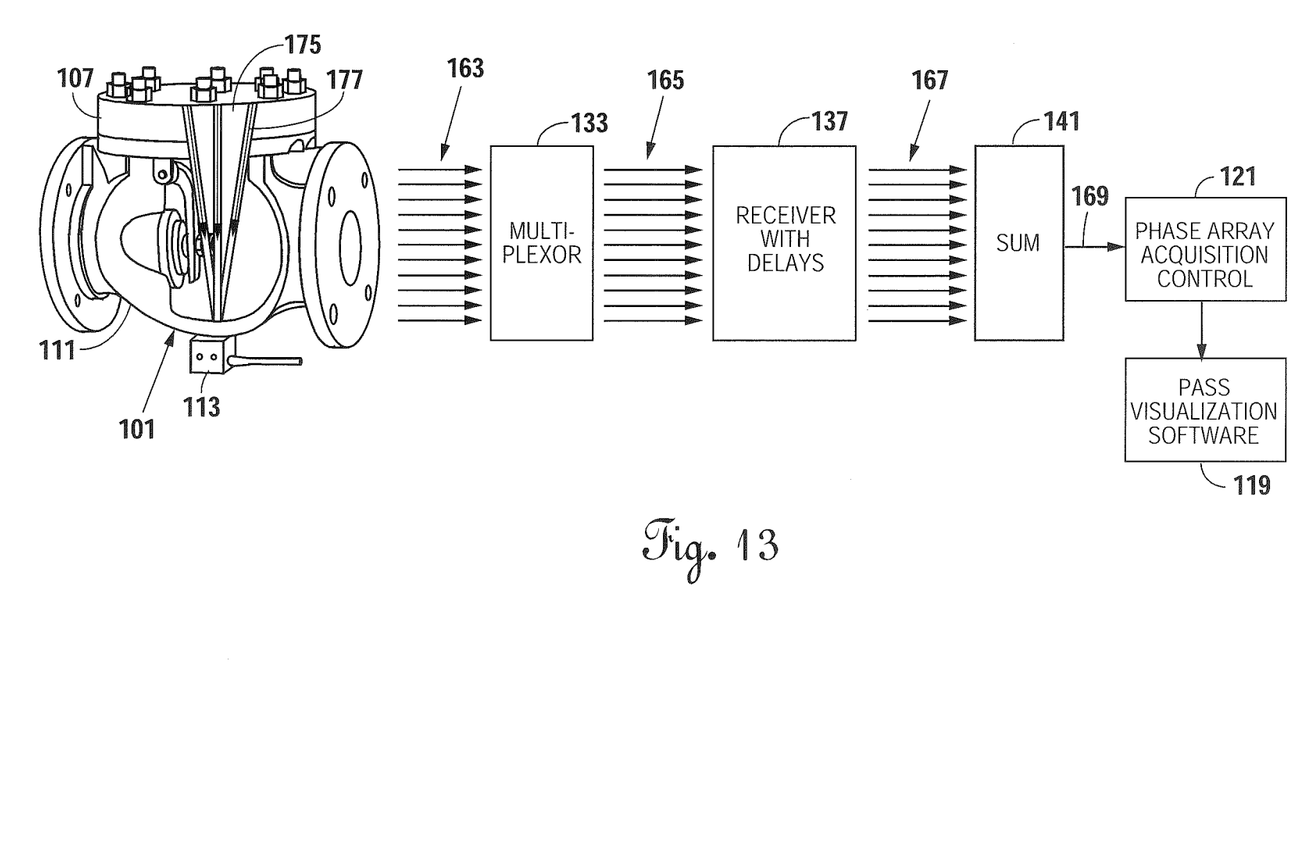
FIG. 13 is a combined pictorial and block diagram illustrating a body probe receiving reflected phase array signals in a swing-type check valve.

FIGS. 12 and 13 are the opposite of FIGS. 10 and 11, where the bonnet probe 109 has been removed and a body probe 113 has been attached. As shown in FIG. 12, the wave front 171 is in the direction of the arrows 173. In FIG. 13, the reflected wave front 175 is in the direction of the arrows 177. Otherwise, everything is the same in FIGS. 12 and 13 as is in FIGS. 10 and 11, respectively.

When the bonnet probe 109 is acting as shown in FIGS. 10 and 11, or the body probe is acting as shown in FIGS. 12 and 13, this is referred to as the "pitch-and-catch" mode. Basically the transmitting probe is also receiving a reflected signal in this "pitch-and-catch" mode. If there is an air pocket, the pitch-and-catch mode would result in a reflected signal being reflected off of the surface of the air pocket. The time of travel of the reflected signal determines exactly where the air pocket is located. The air water interface is what will cause the reflected signal.

Figure 14:
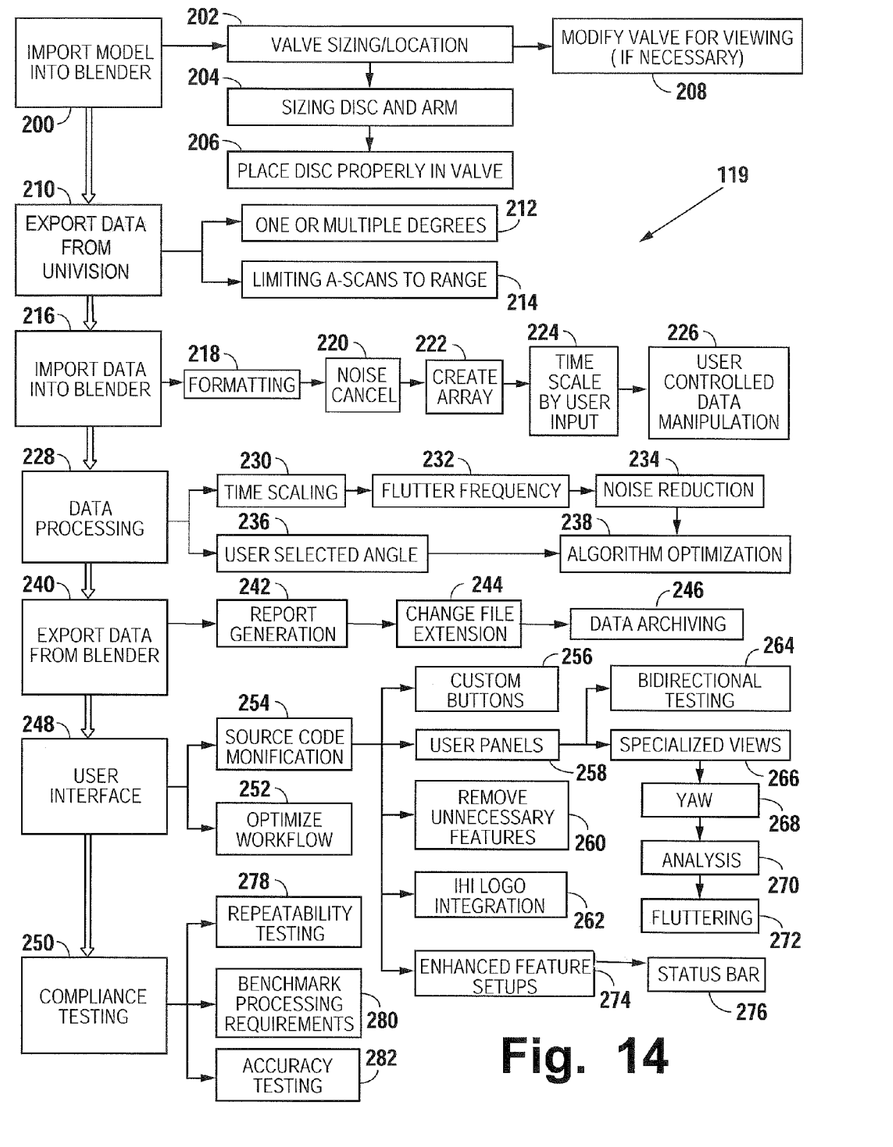
FIG. 14 is a pictorial block diagram of software used to provide visualization of the operation of a swing-type check valve utilizing phase array sequence scanning.

Referring now to FIG. 14, the pass visualization software 119 will be explained in more detail. In the representation shown in FIG. 14, the larger blocks on the left side indicate major steps and the smaller blocks on the right subcomponents of the major steps. During the import model into blender 200, the parametric model of the valve being tested in imported into the pass visualization software 119. As part of the import model into blender 200, valve sizing/location 202 is determined along with sizing disc and arm 204 and if the disc is properly placed in valve 206. Normally, the internal operation of the valve cannot be seen. Therefore, in the pass visualization software 119, a step of modifying the valve for viewing 208 many times will be necessary. In this step, the clapper 103 and hinge 105 (see FIG. 6) will be made visible by cutting away a part of the valve body 111, or make the valve body 111 translucent, so that the clapper 103 can be seen along with its movement. In other words, operation of the valve is made visible for viewing by the operator in modified valve for testing 208.

In the sizing disc and arm 204, the size of the swing-type check valve 101 can be varied to within the constraints of the pass visualization software 109. In other words, the operator could zoom in or out and is limited only by the constraints of the viewing window. In the place disc properly in valve 206, the operator is simply making sure that the disc is properly located inside of the swing-type check valve 101.

In the export data from Univision 210, Univision is the data acquisition software that is being utilized in the present invention, with Univision being the brand name. Data is being exported from Univision software into the pass visualization software 119. The angle is selected at which promulgate the sound waves. The angle determines resolution with each angle interacting with movements of the swing-type check valve 101. Each angle interacts with the movements within the swing-type check valve 101 in different ways. Therefore, during the data collection process, a large number of angles may be used to acquire data during the movement of the clapper 103 in the swing-type check valve 101. For example, the operator may select a 10° angle so that the impinging sound wave would be at 10°. In this manner, the reaction of the clapper being impinged at a 10° sound angle may be evaluated. One of multiple degrees 212 can also be used and data recovered for the multiple degrees 212 of the sound angle. Programs can be selected with one degree or multiple degrees in operating the program.

Also, time of flight of the signal inside of the swing-type check valve 101 may vary depending upon the size of the check valve. Time of flight in a 10 inch diameter check valve will be different than the time of flight in a 20 inch diameter check valve. Therefore, a limiting A-scans to range 214 is set for whatever size check valve is being monitored. Noise beyond the normal time of flight can be cut off so that only the important information is considered.

As the pass visualization software 119 is being set up, open source software may be used. Therefore, an import data into blender 216 is included as the data is being compiled in a compiler and the software being set up. During that step of setting up the software, a number of functions occur such as formatting 218 or determining the number of points that are being imported at a given angle may be included. Also, high resolution or low resolution may be determined by the noise cancel 220, which may occur within the algorithm of the software. For example, the noise signals may be eliminated so that a true reflection signal from the clapper is what will be received. Noise will be anything that is not necessary to the analysis which hopefully could be reduced or eliminated.

After formatting 218 and noise cancel 220, then the create array 222 will determine the array of the data being used to determine movement of the clapper 103 in the swing-type check valve 101 occurs.

Many times the movement of the clapper can be at a high rate of speed that would be invisible to the eye of the operator. Therefore, a time scale by user input 224 is included so that the movement of the clapper can be slowed down in the visualization software 119 so that it can be seen by the operator. The output from the time scale by user input 224 can be manipulated by the operator by user control data manipulation 226. For example, if the clapper 103 is fluttering, the operator through user control data manipulation 226 can make that fluttering appear to be faster or slower. The objective in the time scale by user input 224 and the user control data manipulation 226 is to create a visual representation for the operator in speeds the operator can comprehend.

In the data processing 228, the operator will take the data to see if it's in a format that can be understood by the operator with functions such as time of flight, number of seconds, framing, and resolution. If everything appears to be operating properly, then the operator does not need to make any adjustments. However, that is normally not the case. For example, it may be necessary for time scaling 230, flutter frequency 232 or noise reduction 234. The scale of each of these can be set by the appropriate algorithm.

Simultaneously, the user selected angle 236 is set up so that a particular angle phased array would be used. The number of angles at which the phased array will be presented can be selected by the operator. All of these selected functions are then fed into the algorithm optimization 238, which is used to optimize the information that goes back to the operator.

In export data from blender 240, the motion of the clapper 103 and the swing-type check valve 101 is being replicated in a movie sequence. That is exported through a report generation 242, which active generation has a change file extension 244 prior to data archiving 246. The report generation 242 is what would be signed by check valve engineer indicating that the check valve is working properly. That approved report will then be stored in data archiving 246. By storing the report generation 242 in the data archiving 246, years later someone can come back and see if the swing-type check valve 101 was properly inspected. Also, there is a predictive maintenance tool. Upon viewing the operation of the swing-type check valve 101 as it operates today versus five years from now, the operator can tell if wear is beginning to cause a problem in the swing-type check valve. That is why the change file extension 244 occurs to lock down the data in a particular form.

While it appears that everything is now complete, there are still other major functions such as user interface 248 and compliance testing 250. In the user interface 248, the user could optimize work flow 252 or engage in source code modification 254. It is believed that there may be modifications to the source code based upon feedback by the end user. Things that it are anticipated the end user may want to change would be to insert custom buttons 256, remove unnecessary features 260 or use of the default of IHI logo interrogation 262. Everything to the right of source code modification 254 are various ways the end user can customize their pass visualization software 119. For example, the end user may want to set up their own user panels 258 with bidirectional testing 264 which may be required for swing-type check valves 101 by the regulators. In other words, there must be flow in one direction and attempted flow in the other direction. Also, the user might want specialized views 266, such as yaw 268, analysis 270 or fluttering 272. For example, if the fluttering is extremely fast, the end user may want to have a special view set up concerning the fluttering. All of these custom enhancements the engineer may want to use to determine if the swing-type check valve 101 is operable or needs to be scheduled for maintenance.

Enhanced feature setups 274 allow the user to open data from different valves and analyze them the same way using the same setup. In other words, the end user would set up the software for his particular needs and continue to use it in that manner until it is determined no additional modifications are needed. The status bar 276 simply shows the setup that the end user currently has for his pass visualization software 119.

The object of the user interface 248 and all of the functions from optimized work flow 252 through status bar 276 is to allow the user to set up his pass visualization software in the manner suitable for his needs. This is very similar to someone getting a new computer and setting up the functions in the new computer.

In compliance testing 250, this is to comply with 10 CFR, Appendix B in the Code of Federal Regulations. Since the pass visualization software 119 is being applied in a nuclear power plant, the software must be validated for accuracy, repeatability. Therefore, there is repeatability testing 278, accuracy testing 282 and benchmark processing requirements 280. The bench mark processing requirements 280 is for use by a processor to replicate movement of a swing-type check valve 101 so there can be bench testing. For example, an older type computer may not be able to handle the processing speeds, but a newer, faster computer might be able to handle the speeds. In accuracy testing 282, the accuracy of the system can be determined. For example, if there is 100 cycles/sec. Flutter by the clapper 103 might be represented by two cycles as shown by the operator, but the ratio of the two cycles being equal to 100 cycles needs to be known by the operator.

The object of the pass visualization software 119 is to collect the data in swing-type check valve 101 to show operation of the clapper 103 in a manner that can be readily understood by the operator. For items that are operating at speeds faster than the eye can see such as flutter, those operations will be slowed down so they can be visualized by the operator. Each of the functions that are occurring in swing-type check valve 101 occurs at a speed that can be comprehended by the end user.

What we claim is:

1. A method of testing a check valve while in use, said check valve having a bonnet and a valve body, said testing to (a) determine if said check valve is operating properly and (b) to locate an air pocket, if any, in said check valve, said method comprising the following steps:

attaching piezoelectric devices to at least two water wedges having a reflective index approximately the same as water;

first mounting a first of said water wedges on said bonnet of said check valve;

second mounting a second of said water wedges on said valve body so that said second water wedge generally opposes said first water wedge;

generating a phased array of phased output pulses;

feeding said phased output pulses to multiple channels of said piezoelectric devices attached to said water wedges, said piezoelectric devices having an extra channel;

creating from said phased output pulses an acoustical phased wave front to be transmitted by either (a) said first water wedge or (b) said second water wedge;

receiving said acoustical phased wave front in the other of (a) said first water wedge or (b) said second water wedge and:

(1) if said air pocket is not in said check valve:
   (a) summing said received acoustical phased wave front to give an output;
   (b) first displaying said output to visually indicate condition of said check valve during operation, but;

(2) if said air pocket exists in said check valve:
   (a) receiving a reflected signal from said air pocket on said extra channel at the transmitting water wedge;
   (b) calculating distance to said air pocket by using time of travel of said reflected signal;
   (c) reversing functions of said first water wedge and said second water wedge and repeating steps (2)(a) and (b);
   (d) second displaying location of said air pocket in said check valve.

2. The method of testing a check valve while in use as recited in claim 1 wherein said generating step is via a first multiplexer and a pulser with first delays.

3. The method of testing a check valve while in use as recited in claim 2 wherein said receiving step is via a second multiplexer and a receiver with second delays.

4. The method of testing a check valve while in use as recited in claim 3 wherein said first displaying or said second displaying is through software to provide a visual indication as to the operation of said check valve.

\* \* \* \* \*